(12) United States Patent
Matsuno et al.

(10) Patent No.: US 8,992,548 B2
(45) Date of Patent: Mar. 31, 2015

(54) METHOD FOR LIGATING AN INTERNAL BODY TISSUE

(71) Applicants: Kiyotaka Matsuno, Kanagawa-ken (JP); Takayuki Suzuki, Kanagawa-ken (JP)

(72) Inventors: Kiyotaka Matsuno, Kanagawa-ken (JP); Takayuki Suzuki, Kanagawa-ken (JP)

(73) Assignee: Olympus Corporation (JP)

( * ) Notice: Subject to any disclaimer, the term of this patent is extended or adjusted under 35 U.S.C. 154(b) by 0 days.

(21) Appl. No.: 14/084,138

(22) Filed: Nov. 19, 2013

(65) Prior Publication Data

US 2014/0088615 A1   Mar. 27, 2014

Related U.S. Application Data

(63) Continuation of application No. 11/416,215, filed as application No. PCT/JP2004/016688 on Nov. 4, 2004, now abandoned.

(30) Foreign Application Priority Data

Nov. 5, 2003   (JP) .................................. 2003-375526

(51) Int. Cl.
*A61B 17/12* (2006.01)
*A61B 1/015* (2006.01)
(Continued)

(52) U.S. Cl.
CPC . *A61B 17/12013* (2013.01); *A61B 2017/12018* (2013.01); *A61B 2017/306* (2013.01);
(Continued)

(58) Field of Classification Search
CPC ..................... A61B 2017/12018; A61B 17/12; A61B 17/12009
USPC ........... 606/140, 141, 144, 148; 128/830, 831
See application file for complete search history.

(56) References Cited

U.S. PATENT DOCUMENTS 4,735,194 A   4/1988 Stiegmann
5,356,416 A * 10/1994 Chu et al. ...................... 606/140
(Continued)

FOREIGN PATENT DOCUMENTS

DE   198 27 468 A1   12/1998
EP   0 502 477 A1   3/1992
(Continued)

OTHER PUBLICATIONS

International Search Report PCT/JP2004/016688 dated Jan. 31, 2005.
(Continued)

*Primary Examiner* — Ashley Fishback
*Assistant Examiner* — Jing Ou
(74) *Attorney, Agent, or Firm* — Ostrolenk Faber LLP

(57) ABSTRACT

A method for ligating an internal body tissue using an outer cylinder member and an inner cylinder member including the processes of projecting the inner cylinder from a front end of the outer cylinder member; attaching a ligation band member to an outer peripheral surface of the inner cylinder member; contacting a front end of the inner cylinder member with an internal body tissue; suctioning an inside of the inner cylinder member via a channel communicated with the inside of the inner cylinder member such that the internal body tissue is drawn into the inner cylinder member; and ligating the internal body tissue with the ligation band member by disconnecting the ligation band member from the front end of the inner cylinder member when the inner cylinder member is drawn into the inside the outer cylinder member at a position where the ligation band member is disconnected.

7 Claims, 7 Drawing Sheets

(51) Int. Cl.
    *A61B 17/30*     (2006.01)
    *A61B 1/00*      (2006.01)
    *A61B 17/00*     (2006.01)

(52) U.S. Cl.
    CPC ......... *A61B1/00087* (2013.01); *A61B 1/00089* (2013.01); *A61B 1/00101* (2013.01); *A61B 1/015* (2013.01); *A61B 2017/00296* (2013.01)
    USPC .......................................... 606/140; 606/148

(56)        References Cited

U.S. PATENT DOCUMENTS 5,507,797  A      4/1996  Suzuki et al.
    5,741,273  A      4/1998  O'Regan
    5,788,715  A  *   8/1998  Watson et al. ................ 606/140
    5,833,692  A     11/1998  Cesarini et al.
    5,980,537  A  *  11/1999  Ouchi ........................... 606/140
    6,042,591  A  *   3/2000  Mears ........................... 606/140
    7,166,115  B2 *   1/2007  Suzuki .......................... 606/140
    2003/0229359 A1* 12/2003  Fortier ......................... 606/139

FOREIGN PATENT DOCUMENTS

EP          0 679 368  A1    4/1995
    JP             2958219       7/1999
    JP           2002 526194     8/2002
    WO          WO 97/32528      9/1997

OTHER PUBLICATIONS

Search Report issued by European Patent Office in connection with corresponding application No. EP 04 81 8253 on Apr. 23, 2010.

* cited by examiner

METHOD FOR LIGATING AN INTERNAL BODY TISSUE

CROSS-REFERENCE TO RELATED APPLICATIONS

This application is a continuation application based on U.S. patent application Ser. No. 11/416,215 (now abandoned) filed on May 4, 2006 claiming priority based on Japanese Patent Application No. 2003-375526, filed Nov. 5, 2003. The contents of which are incorporated herein by reference.

BACKGROUND OF THE INVENTION

1. Field of the Invention

The present invention relates to an endoscopic ligation tool and endoscope for ligating a varix that has formed in an internal body tissue, such as the esophagus or stomach.

2. Description of the Related Art

An esophageal varix ligation technique may be used alone or in combination with endoscopic sclerotherapy, in which a sclerosing agent is injected, as a method for treating a varix that has formed in the esophagus or stomach. In this esophageal varix ligation technique, suction is employed to draw the varix toward a cylindrical endoscopic ligation tool attached to the end of the endoscope, and a pre-attached O-ring is released and suspended around the root of the varix. The varix is then mechanically ligated under the elastic force of the O-ring, and thereby obliterated. As an example of this endoscopic ligation tool, a device has been proposed in which an O-ring disposed to the front end of an inner cylinder is disconnected by means of injecting a liquid between the inner and outer cylinders, as disclosed in FIG. 1 of Japanese Patent Publication No. 2958219.

A design has also been proposed as disclosed in FIG. 1 of the Specification of U.S. Pat. No. 4,735,194, or FIG. 2 of Published Japanese translation No. 2002-526194 of International Publication, for example, in which a O-ring is caught on a wire which is inserted into the channel of the endoscope, and the O-ring is then disconnected from the end of the cylindrically shaped member by pulling out the wire.

However, the endoscopic ligation tool according to the first reference (Japanese Patent No. 2958219) is problematic in that it requires the attachment of a supply device and tube along the inserted part of the endoscope for supplying liquid to the endoscopic ligation tool, and the preparations for this are troublesome. Further, in both the endoscopic ligation tool according to the second reference (U.S. Pat. No. 4,735,194) and third reference (Published Japanese translation No. 2002-526194 of International Publication), it is necessary to pass the wire though the channel, so that, in the case where concurrently performing endoscopic sclerotherapy, it is not possible to pass the necessary injection syringe, etc. through the channel. In addition, the devices disclosed in the second and third references are also problematic in that the assembly operations therefore are complicated.

In addition, while the endoscopic ligation tools disclosed in the first and second reference documents do require removal of the endoscope from the body cavity after use, they do not require considerable preparation provided that just the O-ring, or just the inner cylinder with the attached O-ring, can be exchanged. The endoscopic ligation tool according to the third reference is problematic, however, in that once all the O-rings have been used, it is necessary to start all the preparation operations over from the beginning.

The present invention was conceived in view of the above-described circumstances, and has as its objective the provision of an endoscopic ligation tool and endoscope capable of ligating an internal body tissue that has a simple design that does not require a wire or a device for supplying a liquid, this endoscopic ligation tool and endoscope making the aforementioned procedure easier and less time consuming.

SUMMARY OF THE INVENTION

The present invention employs the following means in order to resolve the above-described problems.

According to a first aspect of the invention, a method for ligating an internal body tissue using an outer cylinder member formed in the shape of a cylinder, having a base end configured to attach to and release from an end of an inserted part of an endoscope in which a channel is formed, and an inner cylinder member formed in the shape of a cylinder and being capable of sliding within the outer cylinder member. The method including the processes of: projecting the inner cylinder from a front end of the outer cylinder member; attaching a ligation band member which has annular shape and is configured to freely extend and contract to an outer peripheral surface of the inner cylinder member that projects out from the front end of the outer cylinder member; contacting a front end of the inner cylinder member with an internal body tissue; suctioning an inside of the inner cylinder member via the channel communicated with the inside of the inner cylinder member which is in contact with the internal body tissue so as to form a negative pressure at the inside of the inner cylinder member such that the internal body tissue is drawn into the inner cylinder member and the inner cylinder member slides relative to the outer cylinder member; and ligating the internal body tissue with the ligation band member, by disconnecting the ligation band member from the front end of the inner cylinder member when the inner cylinder member is drawn into the inside the outer cylinder member at a position where the ligation band member is disconnected.

According to a second aspect of the invention, in the method according to the first aspect, the outer cylinder member may have a concave portion which is formed on an inner surface of the outer cylinder member and which has a predetermined length in an axial direction of the outer cylinder member. The inner cylinder member may have a convex portion which is formed on an outer surface of the inner cylinder member and which slidably engages with the inside of the concave portion. The predetermined length may be sufficient to secure a moving distance of the inner cylinder member relative to the outer cylinder member, that is necessary for disconnecting the ligation band member from the inner cylinder member, but limits an excess movement of the inner cylinder. When the inner cylinder member is moved relative to the outer cylinder member, the inner cylinder member may be prevented from being disconnected from the outer cylinder member by sliding the convex portion in the concave portion.

According to a third aspect of the invention, in the method according to the first aspect, may further include adding a sealing agent into a space between the inner cylinder member and the outer cylinder member in order to prevent the inner cylinder member from being disconnected from the outer cylinder member.

According to a fourth aspect of the invention, in the method according to the first aspect, the outer cylinder member and the inner cylinder member may be both formed of a transparent material.

According to a fifth aspect of the invention, in the method according to the second aspect, may furethe include a base being disposed at a base side of the inner cylinder member and has a communicating hole, and an opening space of the communicating hole which is smaller than an inner diameter of said inner cylinder member. The internal body tissue may be attached with the base when suctioning the inside of the inner cylinder member.

According to a sixth aspect of the invention, in the method according to the first aspect, while suctioning the inside of the inner cylinder member, the internal body tissue may be drawn into the inner cylinder member due to suctioning under a first suction pressure, and the inner cylinder member slides relative to the outer cylinder member under a second suction pressure.

According to a seventh aspect of the invention, in the method according to the first aspect, an engaging groove in which said ligation band member is capable of engaging may be formed to the outer peripheral surface of the inner cylinder member.

According to a eighth aspect of the invention, in the method according to the first aspect, in the process of suctioning, may be suction the inside of the inner cylinder member by a suction source that is connected to a proximal end of the channel.

The endoscopic ligation tool according to the present invention is an endoscopic ligation tool for ligating an internal body tissue, provided with: an outer cylinder member formed in the shape of a cylinder, having a base end that can attach to and release from the front end of the inserted part of an endoscope in which a channel is formed; an inner cylinder member formed in the shape of a cylinder, which can project out from the front end of the outer cylinder member and which is capable of sliding movement within the outer cylinder member; and a ligation band member which is annular in shape and freely extends and contracts, that is attached to the outer peripheral surface of the inner cylinder member that projects out from the front end of the outer cylinder member; wherein, when the front end of the inner cylinder member comes into contact with the internal body tissue, the inner cylinder member is moved relative to the outer cylinder member in the direction of the base end of the outer cylinder member, as a result of suction force when the internal body tissue is suctioned via the channel, and the ligation band member can be pushed out by the front end of the outer cylinder member and disconnected.

This endoscopic ligation tool is provided with the above-described design, so that, when the outer cylinder member is attached to the front end of the inserted part of the endoscope, with the inner cylinder member fitted into the outer cylinder member, and the internal body tissue is suctioned, it is possible to seal the front end of the inner cylinder member with the internal body tissue through this suction force. As a result, the internal body tissue can be drawn inside the inner cylinder member. The pressure of the suctioning force on the internal body tissue in this case causes the internal body tissue that has been drawn inside the inner cylinder member to push the inner cylinder member into the outer cylinder member. As a result, the inner cylinder member itself can be drawn into the outer cylinder member, and the front end of the outer cylinder member pushes the ligation band member relatively forward, so that the ligation band member can be disconnected from the front end of the inner cylinder member. As a result, an internal body tissue such as a varix, etc., can be ligated by the ligation band member.

Further, if suctioning is continued even after the front end of the inner cylinder member has been sealed with the internal body tissue, then the suction force increases, and the inner cylinder member itself can be drawn into the outer cylinder member, so that the ligation band member can be disconnected in the same manner as described above.

Accordingly, the operation of taking up an internal body tissue such as a varix or the like into the inner cylinder member and the operation of ligating the tissue by disconnecting the ligation band member can be carried out through a suction operation performed via the channel. In this case, the attachment to the inserted part of the endoscope simply requires fitting of the outer cylinder member, and therefore can be carried out extremely easily. In addition, there is no need to provide a wire member inside the channel as in the conventional art. As a result, other procedure instruments, such as an injection syringe, etc., can be inserted into the channel, even during the ligation operation.

In addition, the endoscopic ligation tool according to the present invention is an endoscopic ligation tool for ligating an internal body tissue, provided with: an outer cylinder member formed in the shape of a cylinder, having a base end that can attach to and release from the front end of the inserted part of an endoscope in which a channel is formed; an inner cylinder member formed in the shape of a cylinder, which can project out from the front end of the outer cylinder member and which is capable of sliding movement within the outer cylinder member; and a ligation band member which is annular in shape and freely extends and contracts, that is attached to the outer peripheral surface of the inner cylinder member that projects out from the front end of the outer cylinder member; wherein, when the front end of the inner cylinder member comes into contact with the internal body tissue, the inner cylinder member is moved relative to the outer cylinder member in the direction of the base end side of the outer cylinder member, due to the pushing force of the inserted part on the internal body tissue, and the ligation band member can be pushed out by the front end of the outer cylinder member, and disconnected.

This endoscopic ligation tool is provided with the above-described design. As a result, by attaching the endoscopic ligation tool to the front end of the inserted part of the endoscope and suctioning the internal body tissue, the inner cylinder member can be drawn into the outer cylinder member by pushing the inner cylinder member into the internal body tissue. Accordingly, the front end of the outer cylinder member pushes the ligation band member in the relatively forward direction, so that the ligation band member can be disconnected from the front end of the inner cylinder member. As a result, an internal body tissue such as a varix, etc., can be ligated using this ligation band member.

Accordingly, the operation of taking up an internal body tissue such as a varix into the inner cylinder member and the operation of ligating the tissue by disconnecting the ligation band member can be carried out continuously. Further, there is no need to provide a wire member or a device for supplying a liquid, so that other procedure instruments, such as an injection syringe, etc., can be inserted into the channel, even during the ligation operation.

In addition, suctioning of the internal body tissue can be accomplished by a different process than required for the disconnection of the ligation band member, making it possible to avoid unintentional disconnection of the ligation band member.

In addition, the endoscopic ligation tool according to the present invention is an endoscopic ligation tool as described above in which a convexly-shaped part is provided projecting out in the radial direction from the inner peripheral surface of the base end side of the inner cylinder member.

This endoscopic ligation tool is provided with the above-described design, so that when the internal body tissue is drawn into the inner cylinder member, the surface of the internal body tissue comes into contact with and pushes against the convexly-shaped part, and generates a force that pushes the inner cylinder member into the outer cylinder member, so that the inner cylinder member can be easily drawn into the outer cylinder member. Accordingly, the ligation band member is pushed out by the front end of the outer cylinder member, and can be pushed out from the front end of the inner cylinder member.

The endoscopic ligation tool according to the present invention is an endoscopic ligation tool as described above, having a floor part in which a communicating hole is formed for connecting the inside with the outside.

This endoscopic ligation tool is provided with the above design, so that when the internal body tissue is drawn into the inner cylinder member, the surface of the internal body tissue comes into contact with and pushes the floor part, and generates a force to push the inner cylinder member into the outer cylinder member, so that the inner cylinder member can be easily drawn into the outer cylinder member. In addition, when the surface of the internal body tissue is suctioned to the point where it is stretched to the floor part, the internal body tissue seals the communicating hole. As a result, a sealed region is formed between the floor part, the internal body tissue, the front end of the inserted part, and the inner surface of the outer cylinder member. In this case, if suctioning is continued further, negative pressure is formed in this region, so that the inner cylinder member can be even more easily drawn into the outer cylinder member. Accordingly, the ligation band member can be pushed out by the front end of the outer cylinder member, and pushed out from the front end of the inner cylinder member under any circumstances.

The endoscopic ligation tool according to the present invention is an endoscopic ligation tool as described above, provided with an anti-disconnect mechanism for preventing the inner cylinder member from disconnecting from the outer cylinder member.

The endoscopic ligation tool according to the present invention is provided with the above design. As a result, it is possible to prevent the inner cylinder member from pulling out from the outer cylinder member and becoming lost.

The endoscopic ligation tool according to the present invention is an endoscopic ligation tool as described above, in which a sealing agent for adjusting the sliding friction is disposed to the space between the inner cylinder member and the outer cylinder member.

The endoscopic ligation tool according to the present invention is provided with the above design. As a result, the frictional resistance between the inner cylinder member and the outer cylinder member is reduced, making it possible to disconnect the ligation band member using suction pressure of a degree required to draw the internal body tissue into the inner cylinder member. Conversely, by employing a sealing agent to increase the frictional resistance, it is possible to prevent the disconnection of the inner cylinder member from the outer cylinder member. In addition, it is also possible to increase air-tightness by filling the space between the inner cylinder member and the outer cylinder member.

The endoscopic ligation tool according to the present invention is an endoscopic ligation tool as described above, in which the outer cylinder member and the inner cylinder member are both formed of a transparent member.

The endoscopic ligation tool according to the present invention is provided with the above design. As a result, it is possible to secure a wide line of vision, facilitate the approach to the lesion site, and carry out the ligation procedure with certainty.

In addition, the endoscopic ligation tool according to the present invention is an endoscopic ligation tool as described above in which an engaging groove in which the ligation band member can engage is formed to the outer peripheral surface of the inner cylinder member.

The endoscopic ligation tool according to the present invention is provided with the above design. As a result, it is possible to prevent the ligation band member from easily disconnecting from the inner cylinder member during times other than when performing the ligation operation.

The endoscope according to the present invention is provided with a pliable inserted part; a channel passing through the inserted part; a suction source that is connected to the base end of the channel and can suction the area outside the front end of the inserted part; and a endoscopic ligation tool according to the present invention provided to the front end of the inserted part.

This endoscope is provided with the above design. As a result, suctioning can be carried out via the channel using the suction source, the inner cylinder member can be relatively moved in a direction such that it is taken up at the base end side of the outer cylinder member, the ligation band member can be pushed out by the front end of the outer cylinder member, and the ligation procedure using the ligation band member can be carried out.

The endoscope according to the present invention is an endoscope as described above, wherein the suction source is designed to provide a suction pressure such that, when the front end of the inner cylinder member and the internal body tissue are adhered together, the internal body tissue can be drawn up into the inner cylinder member, and relative movement of the inner cylinder member with respect to the outer cylinder member is made possible.

This endoscope is provided with the above design. As a result, it is possible to carry out the operation of drawing up a internal body tissue such as a varix or the like, into the inner cylinder member, and the operation of moving the inner cylinder member with respect to the outer cylinder member by manipulating the supply of suction pressure from the suction source, to enable ligation of the varix, etc.

The present invention enables an internal body tissue to be ligated using a simple structure and method, and makes it possible to simplify the technique and reduce the time required for the ligation.

DETAILED DESCRIPTION OF THE INVENTION

The first embodiment of the present invention will now be explained with reference to FIGS. 1 through 6. Note, however, that the present invention is not limited to the following embodiments. For example, it is acceptable to suitably combine the compositional elements in these various embodiments.

Figure 1:
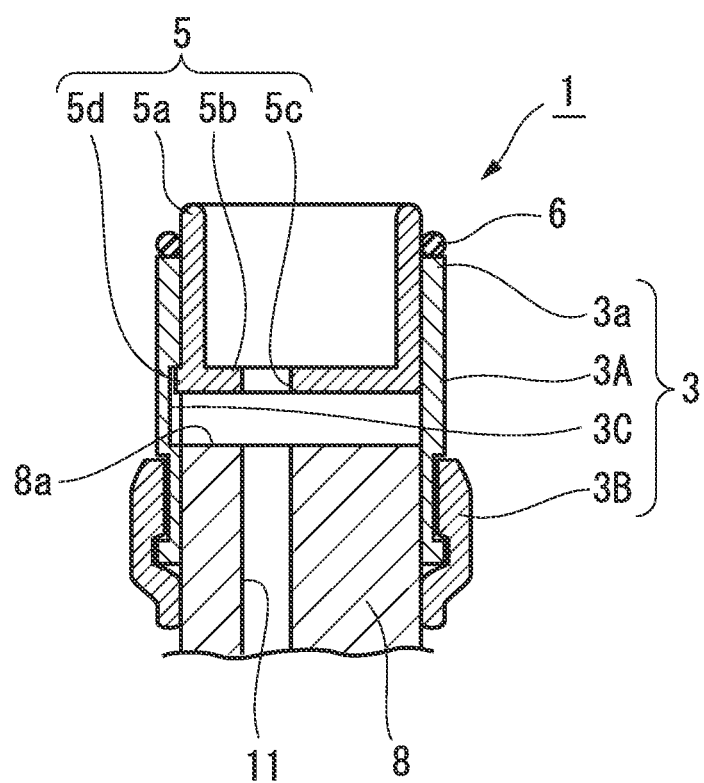
FIG. 1 is a cross-sectional view showing the endoscopic ligation tool according to the first embodiment of the present invention.
Figure 3:
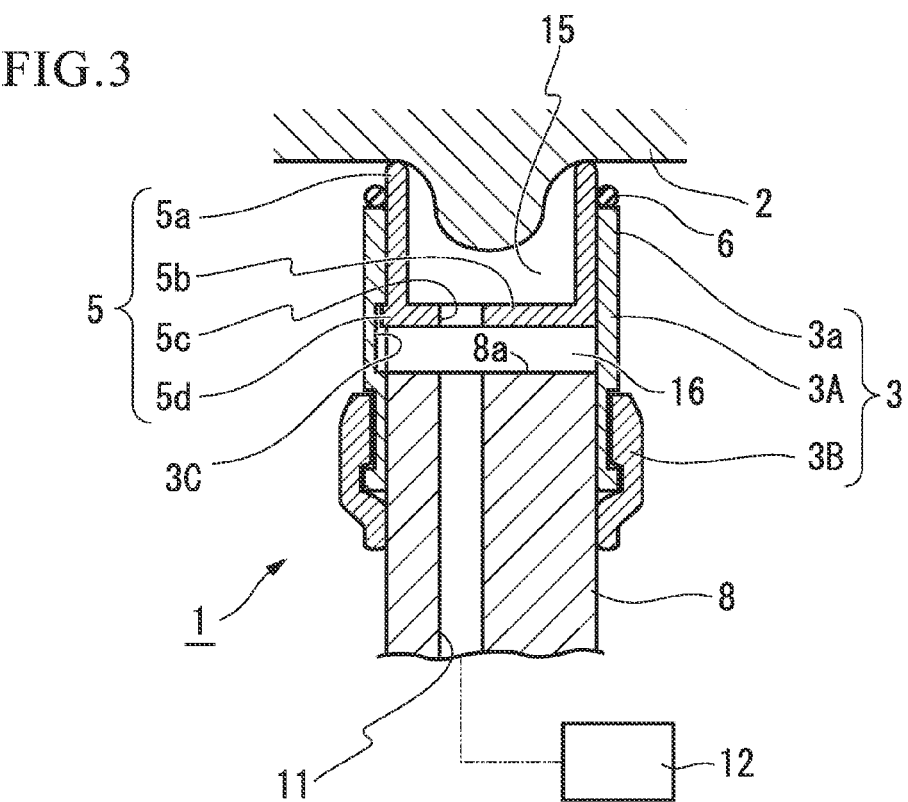
FIG. 3 is an explanatory view showing the arrangement for ligating an internal body tissue using the endoscopic ligation tool according to a first embodiment of the present invention.

The endoscopic ligation tool 1 according to the present embodiment is an endoscopic ligation tool for ligating an esophageal varix or other such internal body tissue 2 (see FIG. 3). As shown in FIG. 1, this endoscopic ligation tool is provided with an outer cylinder member 3, which is formed in the shape of a cylinder; an inner cylinder member 5 which is disposed in a slidable manner within the cylindrically-shaped outer cylinder member 3; and an O-ring (ligating band member) 6 which is annual in shape and can freely extend and contract, that is attached to the outer peripheral surface of the inner cylinder member 5 at the area of the inner cylinder member 5 that projects out from the front end 3a of the outer cylinder member 3.

Figure 2:
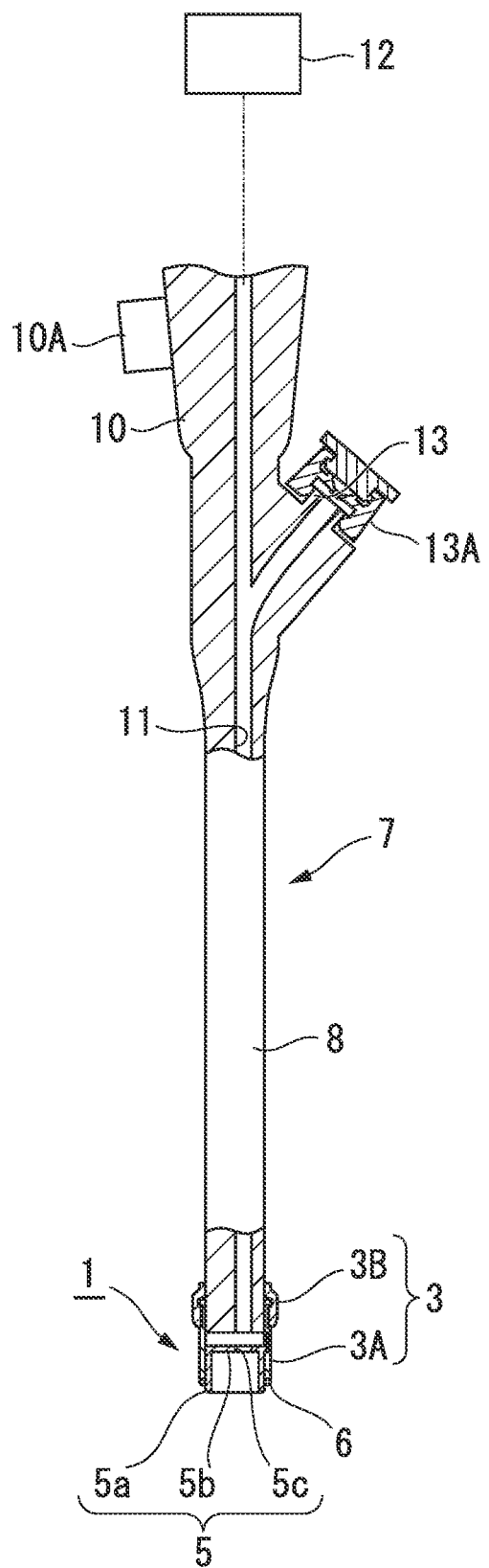
FIG. 2 is a side view including a partial cross-sectional view showing the endoscopic ligation tool according to the first embodiment of the present invention, and an endoscope equipped therewith.

As shown in FIG. 2, the endoscope 7 is provided with a pliable inserted part 8; an endoscope operator 10 that is connected to the base end of the inserted part 8; a channel 11 which passes through the inserted part 8; and a suction device (suction source) 12 that is connected to the base end side of the channel 11 and is capable of suctioning the area outside the front end of the inserted part 8. A forceps port 13 is provided to the base end of the channel 11 for inserting procedure instruments into the channel 11.

As shown in FIG. 1, the outer cylinder member 3 is provided with an outer cylinder main body 3A which is formed of a transparent hard resin, and an attaching part 3B that is connected to the base end of the outer cylinder main body 3A and is formed of a soft resin, and which can be attached to and released from the front end 8a of the inserted part 8 of the endoscope 7 in which the channel 11 shown in FIG. 2 is formed.

The inner cylinder member 5 is designed such that the front end 5a thereof is disposed projecting out in the forward direction from the outer cylinder member 3, a floor part 5b is provided to the base end side thereof, and a communicating hole 5c is formed to the floor part 5b for communicating between the inside and the outside of the inner cylinder member 5.

This inner cylinder member 5 is designed such that the distance between the floor part 5b and the front end 8a of the inserted part 8 is designed to be greater than the distance between the front end 5a of the inner cylinder member 5 and the front end 3a of the outer cylinder member 3, so that the inner cylinder member 5 can be attached to the outer cylinder member 3.

Note that the front end 5a of the inner cylinder member 5 is formed into a round shape in order to increase adherence with the internal body tissue 2.

A concave part (anti-disconnect mechanism) 3C is formed to the inner peripheral surface of the outer cylinder member 3 extending in the axial direction from the base end of the outer cylinder main body 3A to the front end 3a side, and a convex part (anti-disconnect mechanism) 5d is provided to the outer periphery of the floor part 5b of the inner cylinder member 5 for engaging with the concave part 3C in a manner to enable sliding in the axial direction. The length of this concave part 3C is sufficient to secure the relative moving distance between the inner cylinder member 5 and the outer cylinder member 3 that is necessary to enable disconnection of the O-ring 6, but restrict movement in excess of this amount.

A sealing agent such as silicon or the like is coated in between the inner cylinder member 5 and the outer cylinder member 3, so that the O-ring 6 can be disconnected using suction pressure of a degree needed to draw the internal body tissue 2 inside the inner cylinder member 5 by decreasing the sliding friction so that inner cylinder member 5 moves easily within the outer cylinder member 5.

A suction device 12 is equipped with a vacuum pump as the suction source, and is designed to be able to provide a suctioning pressure such that, when the front end of the inner cylinder member 5 and the internal body tissue 2 are made to adhere and the suction button 10A is pushed, the internal body tissue 2 is drawn into the inner cylinder member 5 and the inner cylinder member 5 is able to slide relatively with respect to the outer cylinder member 3 under the control of a controller which is not shown in the figures.

Note that this suction button 10A can be designed to be depressed in two stages. Namely, it is acceptable to provide a suction button 10A in which, by depressing the button to the first stage, the internal body tissue 2 is drawn into the inner cylinder member 5 due to suctioning under a first suction pressure. If the button is then further depressed from this first stage, the inner cylinder member 5 is moved relative to the outer cylinder member 3 under the second suction pressure, and O-ring 6 can be disconnected.

Next, the method for operating the endoscopic ligation tool 1 and the endoscope 7 according to this embodiment, and the actions and effects thereof, will be explained.

First, the inner cylinder member 5 is inserted into the outer cylinder main body 3A so that the floor part 5b is the base end side of the outer cylinder member 3, causing engagement between the concave part 3C and the convex part 5d. Next, the front end 5a of the inner cylinder member 5 is made to project out from the front end 3a of the outer cylinder member 3, and the O-ring 6 is attached to the outer peripheral surface of the outwardly-projecting inner cylinder member 5. As a result, the positioning of the inner cylinder member 5 in the outer cylinder member 3 is determined as a result of the restriction of the distance that the inner cylinder member 5 can move with respect to the outer cylinder member 3.

Next, the endoscopic ligation tool 1 is attached by covering the outer peripheral surface of the front end 8a of the inserted part 8 of the endoscope 7 that projects out from the front end of the outer cylinder member 3 by the attaching part 3B. The inserted part 8 of the endoscope 7 is then inserted in this state into the esophagus, and moved to the varix or other such internal body tissue 2, so that the front end 5a of the inner cylinder member 5 comes into contact with the surface of the internal body tissue 2.

At this point, a sealed first region 15 enclosed by the internal body tissue 2 and the inner cylinder member 5, and a second region 16 enclosed by the floor part 5b, the front end 8a of the inserted part 8, and the outer cylinder member 3, are formed as shown in FIG. 3.

The suction button 10A is then depressed. The vacuum pump of the suction device 12 is activated under the control of a controller for suctioning the inside of the inner cylinder member 5 and to create a negative pressure in the first region 15 via the channel 11. And then, the internal body tissue 2 is drawn into the inner cylinder member 5 and the inner cylinder member 3 slides relative to the outer cylinder member 3.

Next, the process of ligating the internal body tissue with the O-ring 6, and by disconnecting the O-ring 6 from the front end of the inner cylinder member 5 when the inner cylinder member 5 is drawn into the inside the outer cylinder member 3 at a position where the ligation band member is disconnected.

Figure 4:
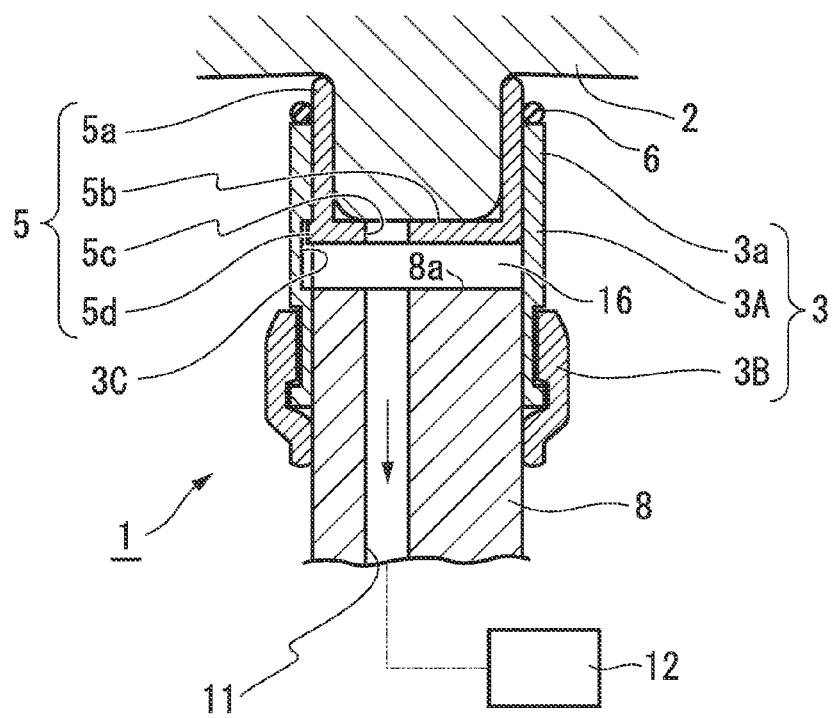
FIG. 4 is an explanatory view showing the arrangement for ligating an internal body tissue using the endoscopic ligation tool according to a first embodiment of the present invention.
Figure 5:
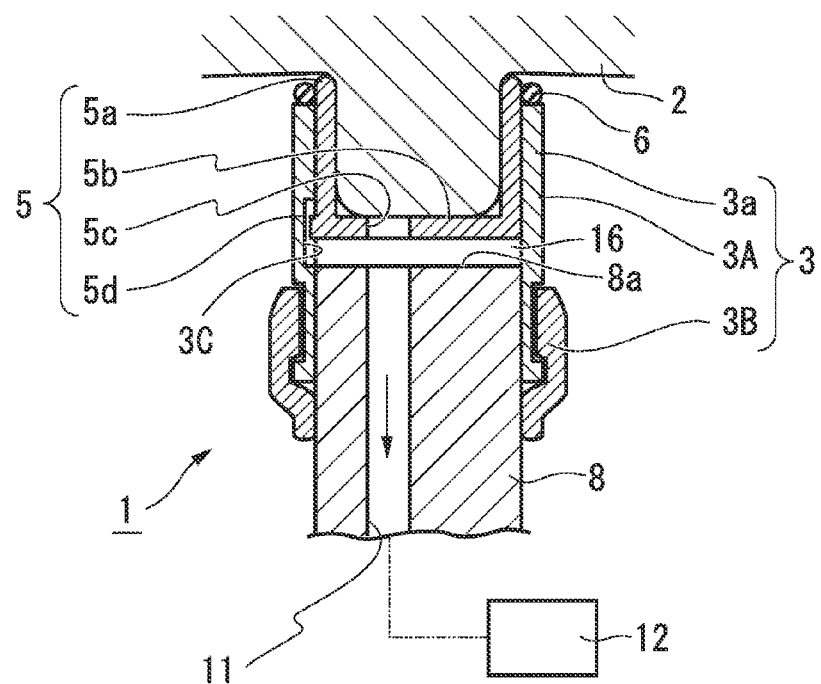
FIG. 5 is an explanatory view showing the arrangement for ligating an internal body tissue using the endoscopic ligation tool according to a first embodiment of the present invention.

The front end 5a of the inner cylinder member 5 is then sealed by the internal body tissue 2, and the internal body tissue 2 is further drawn up into the inner cylinder member 5. Next, as shown in FIG. 4, the communicating hole 5c becomes blocked by the internal body tissue 2, so that a sealed state is created in the second region 16. A region of negative pressure is then created in this second region 16. In this case, the O-ring 6, which is attached to the front end 5a of the inner cylinder member 5, is pushed forward by the front end 3a of the outer cylinder member 3 accompanying the movement of the inner cylinder member 5 relative to the base end side of the outer cylinder member 3, as shown in FIG. 5.

Figure 6:
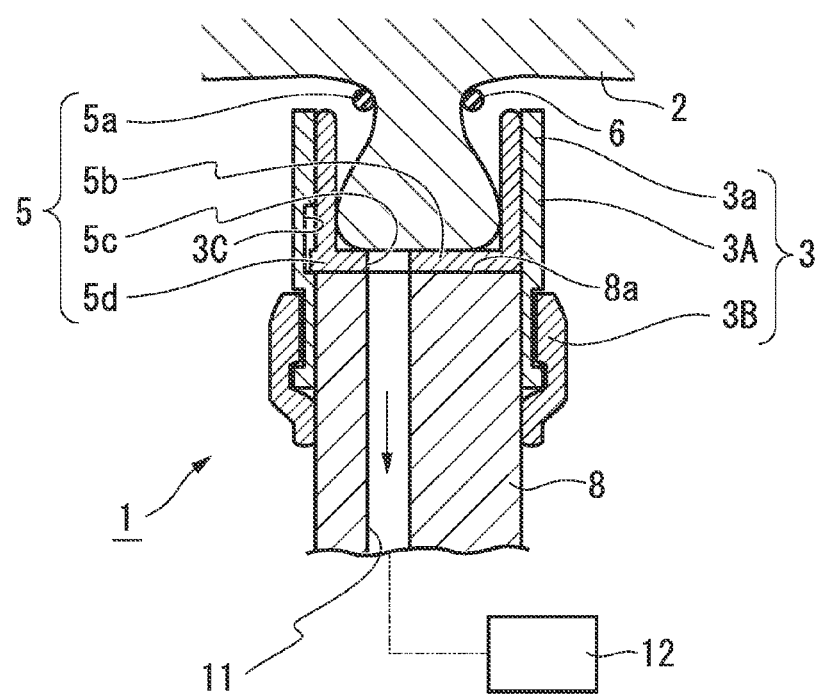
FIG. 6 is an explanatory view showing the arrangement for ligating an internal body tissue using the endoscopic ligation tool according to a first embodiment of the present invention.

As shown in FIG. 6, the O-ring 6 is disconnected from the inner cylinder member 5, ligating the varix or other such internal body tissue 2.

When the suction pump 10A is released, the internal body tissue 2 separates from the inner cylinder member 5. However, since the distance that the inner cylinder member 5 can move is limited by the concave part 3C and the convex part 5d, the inner cylinder member 5 becomes housed inside the outer cylinder member 3.

In the case when ligating another internal body tissue, the inserted part 8 is first removed to the outside of the body. At this point, an O-ring 6 can be attached to the front end 5a of the inner cylinder member 5 by causing the inner cylinder 5 to project out from within the outer cylinder member 3, or, the inner cylinder member 5 may be removed from the outer cylinder member 3 and a new inner cylinder member 5 with an attached O-ring 6 can be exchanged by applying pressure from the front end of the outer cylinder member 3. Alternatively, a new endoscopic ligation tool 1 can be provided. The same operation as described above is then carried out again.

As a result of this endoscopic ligation tool 1 and endoscope 7, it is possible to continuously carry out the operation of taking up a varix or other such internal body tissue 2 into the inner cylinder member 5, and the operation of ligating the tissue with the O-ring 6, using the suction force from the suction device 12. Accordingly, the need to provide a wire member inside the channel 11 as in the conventional art is eliminated. As a result, other procedure instruments such as injection syringes, etc. can be passed through the channel 11, making it possible to carry out endoscopic sclerotherapy in a continuous manner. In addition, by means of the concave part 3C and the convex part 5d, it is possible to prevent the inner cylinder member 5 from being pulled out from the outer cylinder member 3 and becoming lost following ligation with the O-ring 6.

Further, since both the outer cylinder member 3 and the inner cylinder member 5 are transparent, it is possible to ensure a wide line of view, facilitating approach to the internal body tissue 2 that includes the lesion site. As a result, it is possible to carry out the ligation procedure with certainty.

Figure 7:
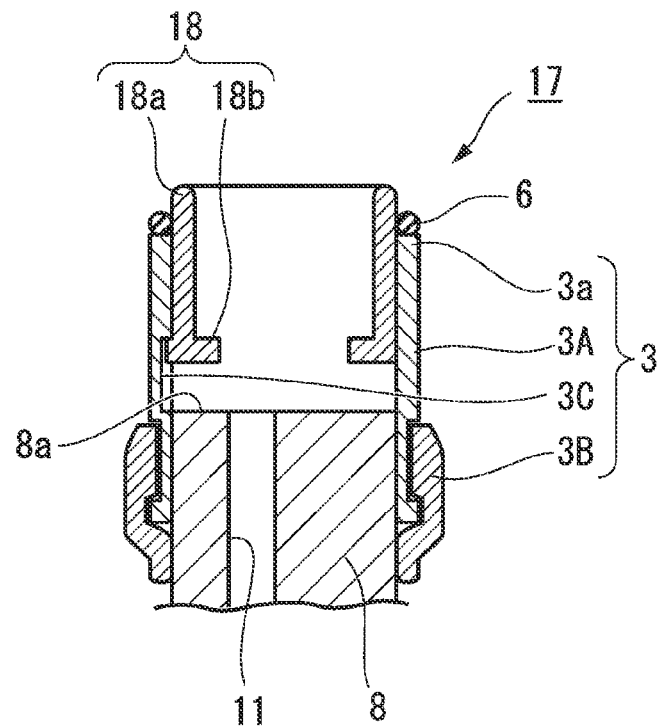
FIG. 7 is a cross-sectional view showing the endoscopic ligation tool according to a second embodiment of the present invention.

Next, a second embodiment of the present invention will be explained with reference to FIG. 7. Note that compositional elements that are equivalent to those of the first embodiment will be assigned the same numeric symbol and an explanation thereof will be omitted here.

The point of difference between the second embodiment and the first embodiment is that a floor part 5b, having a communicating hole 5c formed in its base end, is provided to the inner cylinder member 5 of the endoscopic ligation tool 1 according to the first embodiment. In contrast, a convexly-shaped part 18b that projects out in the radial direction from the inner peripheral surface of the inner cylinder member 18 of the endoscopic ligation tool 17 is provided in this second embodiment.

Next, the method for operating the endoscopic ligation tool 17 and endoscope 7, and the actions and effects thereof, will be explained.

In the same manner as in the first embodiment, this endoscopic ligation tool 17 is attached to the front end of the inserted part 8, and inserted inside a body cavity, after which it is employed to suction the internal body tissue 2 using the suction device 12. In this case, the surface of the suctioned internal body tissue 2 is drawn into the inner cylinder member 18 under the suctioning force of the suction device 12, until the internal body tissue 2 comes into contact with the convexly-shaped part 18b. At this point, the surface of the internal body tissue 2 can generate force via the convexly-shaped part 18b to push the inner cylinder member 18 inside the outer cylinder member 3. Due to this force, the inner cylinder member 18 can be easily drawn inside the outer cylinder member 3. Accordingly, the O-ring 6 is pushed out by the front end of the outer cylinder member 3, and can be pushed out from the front end 18a of the inner cylinder member 18.

Note that the scope of the present invention is not limited to the embodiments described above. Rather, various alternations may be added within a range that does not depart from the spirit of the invention.

Figure 8:
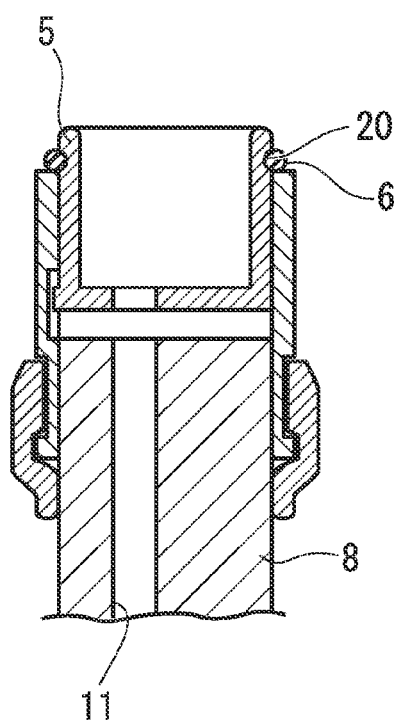
FIG. 8 is a cross-sectional view showing the endoscopic ligation tool according to another embodiment of the present invention.

As shown in FIG. 8, for example, it is acceptable to form an engaging groove 20, capable of engaging the O-ring 6, in the outer peripheral surface of the inner cylinder member 5.

In this case, it is possible to prevent the O-ring 6 from disconnecting from the inner cylinder member 5 at times other than during the ligation operation, and to enable the ligation operation to be carried out in a stable state.

In addition, it is also acceptable to not only restrict the distance of movement between the inner cylinder member 5 and the outer cylinder member 3 by means of the concave part 3C and the convex part 5d, but also to provide a sealing agent for increasing the sliding friction between the inner cylinder member 5 and the outer cylinder member 3.

In this case, it is possible to prevent the inner cylinder member 5 from disconnecting from the outer cylinder member 3 by increasing the frictional resistance between the inner cylinder member 5 and the outer cylinder member 3.

Figure 9:
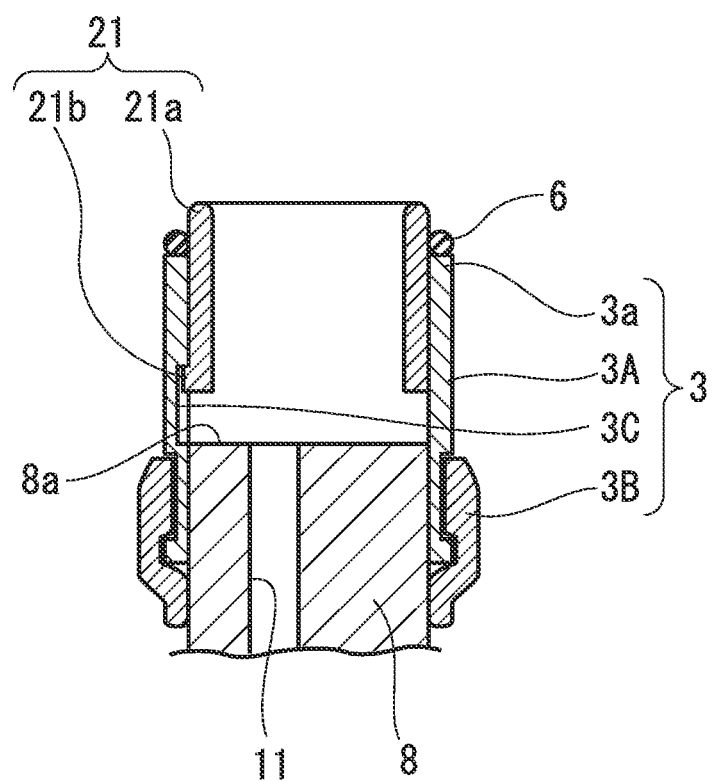
FIG. 9 is a cross-sectional view showing the endoscopic ligation tool according to another embodiment of the present invention.

In addition, as shown in FIG. 9, it is also acceptable to provide an inner cylinder member 21 in which there is no floor part 5b or convexly-shaped part 18b.

In this case, the front end 21a of the inner cylinder member 21 is brought into contact with and suctions the internal body tissue, so that the internal body tissue is drawn up inside inner cylinder member 21. When suctioning is further continued in this state, the suctioning pressure increases, and the inner cylinder member 21 itself can be drawn up inside the outer cylinder member 3. The front end of the outer cylinder member 3 pushes the O-ring 6 relatively toward the front end 21a of the inner cylinder member 21, so that the O-ring 6 can be disconnected from the front end 21a of the inner cylinder member 21.

Figure 10:
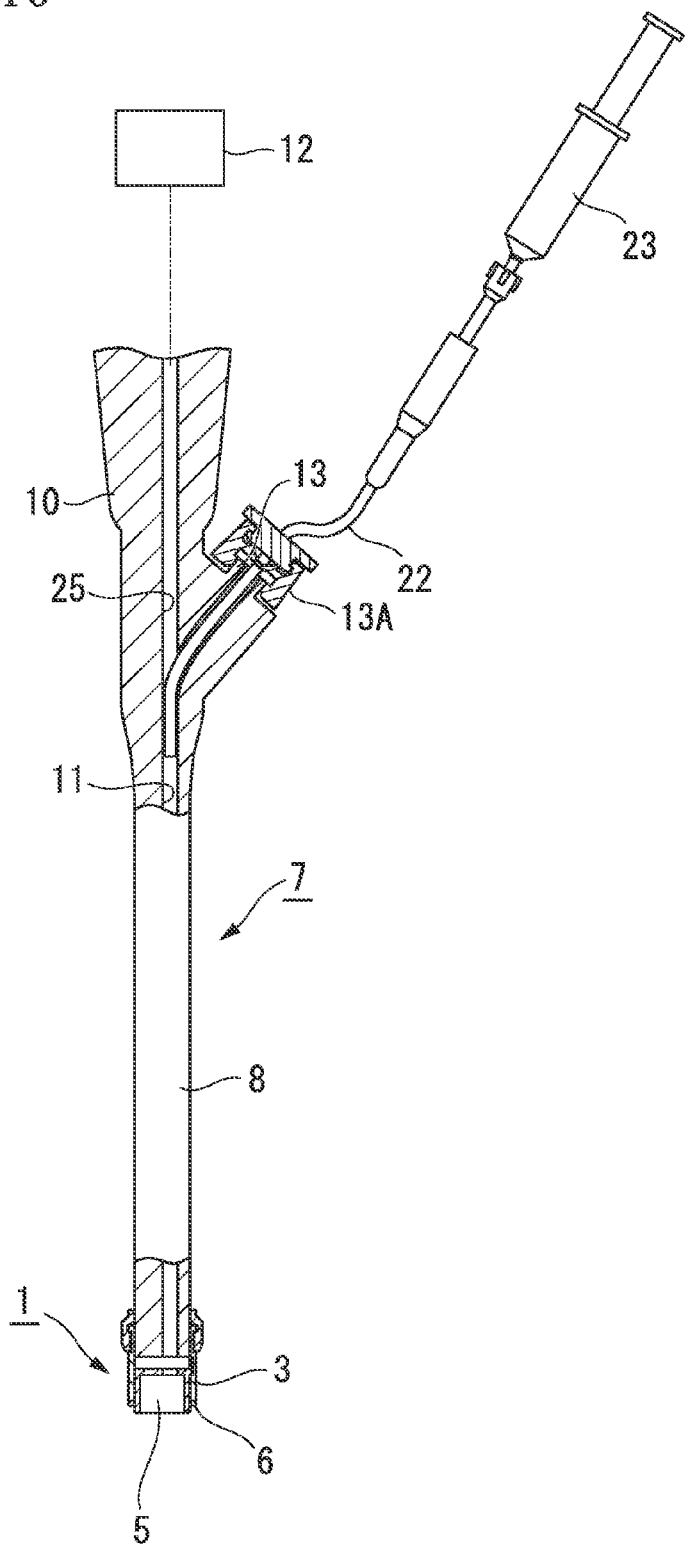
FIG. 10 is a side view including a partial cross-sectional view showing the endoscopic ligation tool according to another embodiment of the present invention, and an endoscope equipped therewith.

In the preceding embodiment, the suction device 12 of the endoscope 7 was employed as the suction source. However, it is also acceptable to provide a syringe 23 that has a tube 22, insertable into the channel 11, connected at its end, for the suction source, as shown in FIG. 10.

In this case, the front end of the tube 22 extends from the position where the channel 11 and a branching tube 25, which is connected to the suction device 12, branch, to the front end side of the channel 11. As a result, it is possible to prevent the flow of air into the branched tube 25 during the ligation operation, and to carry out the operation using syringe 23 with accuracy.

The endoscopic ligation tool is attached to the front end of the inserted part 8 of the endoscope 7 and the internal body tissue 2 is suctioned. By then pushing the inner cylinder member into the internal body tissue 2, the inner cylinder member can be drawn into the outer cylinder member. In this case, the front end of the outer cylinder member enters a state such that it is pushing the O-ring 6 in the forward direction relatively, so that the O-ring 6 can be disconnected from the front end of the inner cylinder member. As a result, it is possible to ligate a varix or other such internal body tissue with the O-ring 6.

In this case, the internal body tissue 2 can be suctioned by means of an operation different from that used to disconnect the O-ring 6, making it possible to prevent unintentional disconnection of the O-ring 6.

The prevent invention can be employed as an endoscopic ligation tool and endoscope for ligating a varix that has formed in an internal body tissue such as the esophagus or stomach.

The present invention makes it possible to ligate an internal body tissue using a simple design and method, and enables the procedure to be made simpler and faster.

While preferred embodiments of the invention have been described and illustrated above, it should be understood that these are exemplary of the invention and are not to be considered as limiting. Additions, omissions, substitutions, and other modifications can be made without departing from the scope of the present invention. Accordingly, the invention is not to be considered as being limited by the foregoing description, and is only limited by the scope of the appended claims.

What is claimed is:

1. A method for ligating an internal body tissue using an outer cylinder member formed in the shape of a cylinder, having a base end configured to attach to and release from an end of an inserted part of an endoscope in which a channel is formed, and an inner cylinder member formed in the shape of a cylinder and being capable of sliding within the outer cylinder member, the method comprising the processes of:
projecting the inner cylinder from a front end of the outer cylinder member;
attaching a ligation band member which has annular shape and is configured to freely extend to an outer peripheral surface of the inner cylinder member that projects out from the front end of the outer cylinder member;
contacting a front end of the inner cylinder member with an internal body tissue;
suctioning an inside of the inner cylinder member via the channel communicated with the inside of the inner cylinder member which is in contact with the internal body tissue so as to form a negative pressure at the inside of the inner cylinder member such that the internal body tissue is drawn into the inner cylinder member and the inner cylinder member slides relative to the outer cylinder member; and
ligating the internal body tissue with the ligation band member, by disconnecting the ligation band member from the front end of the inner cylinder member when the inner cylinder member is drawn into the inside the outer cylinder member at a position where the ligation band member is disconnected, wherein
while suctioning the inside of the inner cylinder member, the internal body tissue is drawn into the inner cylinder member due to suctioning under a first suction pressure by depressing a suction button, and the inner cylinder member slides relative to the outer cylinder member to disconnect the ligation band member from the front end of the inner cylinder member solely by a second higher suction pressure.

2. The method for ligating an internal body tissue according to claim 1, wherein
the outer cylinder member has a concave portion which is formed on an inner surface of the outer cylinder member and which has a predetermined length in an axial direction of the outer cylinder member,
the inner cylinder member has a convex portion which is formed on an outer surface of the inner cylinder member and which slidably engages with the inside of the concave portion,
the predetermined length is sufficient to secure a moving distance of the inner cylinder member relative to the outer cylinder member, that is necessary for disconnecting the ligation band member from the inner cylinder member, but limits an excess movement of the inner cylinder, and
when the inner cylinder member is moved relative to the outer cylinder member, the inner cylinder member is prevented from being disconnected from the outer cylinder member by sliding the convex portion in the concave portion.

3. The method for ligating an internal body tissue according to claim 2, further comprising,
a base being disposed at a base side of the inner cylinder member and having a communicating hole, and
an opening space of the communicating hole which is smaller than an inner diameter of said inner cylinder member, wherein
the internal body tissue is attached with the base when suctioning the inside of the inner cylinder member.

4. The method for ligating an internal body tissue according to claim 1, further comprising,
adding a sealing agent into a space between the inner cylinder member and the outer cylinder member in order to prevent the inner cylinder member from being disconnected from the outer cylinder member.

5. The method for ligating an internal body tissue according to claim 1, wherein
the outer cylinder member and the inner cylinder member are both formed of a transparent material.

6. The method for ligating an internal body tissue according to claim 1, wherein
an engaging groove in which the ligation band member is capable of engaging is formed to the outer peripheral surface of the inner cylinder member.

7. The method for ligating an internal body tissue according to claim 1, wherein in the process of suctioning, suctioning the inside of the inner cylinder member by a suction source that is connected to a proximal end of the channel.

* * * * *